(12) United States Patent
Stone

(10) Patent No.: US 8,969,058 B2
(45) Date of Patent: Mar. 3, 2015

US008969058B2

(54) METHOD FOR RELEASING GENETIC MATERIAL FROM SOLID PHASE

(75) Inventor: Michele R. Stone, Rockville, MD (US)

(73) Assignee: Canon U.S. Life Sciences, Inc., Rockville, MD (US)

(*) Notice: Subject to any disclaimer, the term of this patent is extended or adjusted under 35 U.S.C. 154(b) by 726 days.

(21) Appl. No.: 12/334,952

(22) Filed: Dec. 15, 2008

(65) Prior Publication Data

US 2009/0093036 A1 Apr. 9, 2009

Related U.S. Application Data

(62) Division of application No. 11/946,687, filed on Nov. 28, 2007, now abandoned.

(60) Provisional application No. 60/867,699, filed on Nov. 29, 2006.

(51) Int. Cl.
*C12N 13/00* (2006.01)
*G01N 1/40* (2006.01)

(52) U.S. Cl.
CPC ........ *G01N 1/405* (2013.01); *G01N 2001/4094* (2013.01)
USPC .............. 435/173.1; 435/173.4; 435/173.7; 435/173.9; 204/157.15; 204/157.62; 204/158.2; 204/158.21

(58) Field of Classification Search
USPC .............................. 435/173.1, 173.4, 173.9, 6
See application file for complete search history.

(56) References Cited

U.S. PATENT DOCUMENTS

| | | | |
|---|---|---|---|
| 3,558,066 A * | 1/1971 | Alliger .............................. 241/2 |
| 3,713,987 A * | 1/1973 | Low .......................... 435/309.1 |
| 4,187,556 A | 2/1980 | Jones |
| 4,358,535 A | 11/1982 | Falkow et al. |
| 4,797,355 A | 1/1989 | Stabinsky |
| 5,234,809 A | 8/1993 | Boom et al. |
| 5,237,016 A | 8/1993 | Ghosh et al. |
| 5,374,522 A * | 12/1994 | Murphy et al. .............. 435/6.16 |
| 5,496,562 A | 3/1996 | Burgoyne |
| 5,580,575 A | 12/1996 | Unger et al. |
| 5,652,141 A | 7/1997 | Henco et al. |
| 5,756,126 A | 5/1998 | Burgoyne |
| 5,759,369 A | 6/1998 | Menchen et al. |
| 5,807,527 A | 9/1998 | Burgoyne |
| 5,910,246 A | 6/1999 | Walter et al. |
| 6,274,726 B1 * | 8/2001 | Laugharn et al. ............ 536/25.4 |
| 6,322,983 B1 | 11/2001 | Burgoyne |
| 6,410,725 B1 | 6/2002 | Scholl et al. |
| 6,617,105 B1 | 9/2003 | Rudi et al. |
| 6,627,226 B2 | 9/2003 | Burgoyne et al. |
| 6,645,717 B1 | 11/2003 | Smith et al. |
| 6,746,841 B1 | 6/2004 | Fomovskaia et al. |
| 6,878,540 B2 | 4/2005 | Pourahmadi et al. |
| 6,881,541 B2 | 4/2005 | Petersen et al. |
| 6,972,329 B2 | 12/2005 | Burgoyne |
| 7,214,780 B2 | 5/2007 | Cunningham et al. |
| 7,217,513 B2 | 5/2007 | Parameswaran et al. |
| 7,294,489 B2 | 11/2007 | Brentano et al. |
| 2001/0039014 A1 | 11/2001 | Bass et al. |
| 2002/0186869 A1 * | 12/2002 | Neriishi ........................ 382/129 |
| 2003/0019791 A1 * | 1/2003 | Austin ......................... 208/106 |
| 2003/0054383 A1 | 3/2003 | Bass et al. |
| 2003/0054384 A1 | 3/2003 | Bass et al. |
| 2003/0064393 A1 | 4/2003 | Bass et al. |
| 2003/0077839 A1 | 4/2003 | Takei |
| 2004/0253584 A1 | 12/2004 | Ihle et al. |
| 2004/0265871 A1 | 12/2004 | Angelsen et al. |
| 2006/0024712 A1 | 2/2006 | Baker et al. |
| 2007/0170812 A1 | 7/2007 | Fani et al. |
| 2008/0020380 A1 | 1/2008 | Patno et al. |

FOREIGN PATENT DOCUMENTS

WO 9112079 A 8/1991

OTHER PUBLICATIONS

Rantakokko-Jalava et al., "Optimal DNA Isolation Method for Detection of Bacteria in Clinical Specimens by Broad-Range PCR," J. Clinical Microbiology, 40(11):4211-4217 (2002).

Fahle et al., "Comparison of Six Commercial DNA Extraction Kits for Recovery of Cytomegalovirus DNA from Spiked Human Specimens," J. Clin. Microbiology, 38(10):3860-3863 (2000).

\* cited by examiner

*Primary Examiner* — Allison Fox
*Assistant Examiner* — Susan E Fernandez
(74) *Attorney, Agent, or Firm* — Rothwell, Figg, Ernst & Manbeck, P.C.

(57) ABSTRACT

The present invention relates to systems for releasing genetic materials from a solid medium. The present invention also relates to methods for releasing genetic materials from a solid medium. The present invention further relates to methods for isolating genetic material from a biological sample.

22 Claims, 5 Drawing Sheets

METHOD FOR RELEASING GENETIC MATERIAL FROM SOLID PHASE

This application is a divisional of application Ser. No. 11/946,687, filed on Nov. 28, 2007, which claims the benefit of Provisional Patent Application No. 60/867,699, filed on Nov. 29, 2006, which is incorporated herein by this reference in its entirety.

BACKGROUND OF THE INVENTION

1. Field of the Invention

The present invention relates to systems for releasing genetic materials from a solid medium. The present invention also relates to methods for releasing genetic materials from a solid medium. The present invention further relates to methods for isolating genetic material from a biological sample.

2. Description of the Related Art

Genetic material in blood samples, tissue samples and other fluids is used for the purposes of monitoring and diagnosing genetic diseases, blood-borne parasitic diseases such as malaria, and other diseases and disorders. Genetic material further can be used for determining paternity and monitoring other unusual cell populations in blood and other fluids. Analysis of genetic material can be achieved through numerous techniques and utilizes various materials. Generally, these techniques and methods involve the initial collection of the genetic material, storage of the genetic material and then subsequent analysis of the genetic material.

Human genomic DNA is purified by a variety of methods (Sambrook and Russell (2001), *Molecular Cloning*, 3rd Ed., Cold Spring Harbor Laboratory Press, Cold Spring Harbor, N.Y.; Ausubel et al. (1992), *Current Protocols in Molecular Biology*, John Wiley & Sons, New York, including periodic updates). Consequently, many commercial kit manufacturers provide products for such techniques, for example: AmpReady™ (Promega, Madison, Wis.), DNeasy™ (Qiagen, Valencia, Calif.), and Split Second™ (Roche Molecular Biochemicals, Indianapolis, Ind.). These products rely on the use of specialized matrices or buffer systems for the rapid isolation of the genomic DNA molecule.

More recently, microporous filter-based techniques have surfaced as tools for the purification of genomic DNA as well as a whole multitude of nucleic acids. The advantages of filter-based matrices are that they can be fashioned into many formats that include tubes, spin tubes, sheets, and microwell plates. Microporous filter membranes as purification support matrices have other advantages within the art. They provide a compact, easy to manipulate system allowing for the capture of the desired molecule and the removal of unwanted components in a fluid phase at higher throughput and faster processing times than possible with column chromatography. This is due to the fast diffusion rates possible on filter membranes.

Nucleic acid molecules have been captured on filter membranes, generally either through simple adsorption or through a chemical reaction between complementary reactive groups present on the filter membrane or on a filter-bound ligand resulting in the formation of a covalent bond between the ligand and the desired nucleic acid.

Porous filter membrane materials used for non-covalent nucleic acid immobilization have included materials such as nylon, nitrocellulose, hydrophobic polyvinylidinefluoride (PVDF), and glass microfiber. A number of methods and reagents have also been developed to also allow the direct coupling of nucleic acids onto solid supports, such as oligonucleotides and primers (e.g., Coull et al. (1986), *Tetrahedron Lett* 27:3991-3994; Connolly (1987), *Nucleic Acids Res* 15:3131-3139, 1987; Connolly and Rider (1985), *Nucleic Acids Res* 12:4485-4502; Yang et al. (1998), *Proc Natl Acad Sci USA* 95:5462-5467). UV cross-linking of DNA (Church et al. (1984), *Proc Natl Acad Sci USA* 81:1991-1995), RNA (Khandjian et al. (1986), *Anal Biochem* 159:227-232) to nylon membranes, The Generation Capture Column Kit (Qiagen, Valencia, Calif.) QIAamp DNA Blood Mini Kit, QIAamp DNA Mini Kit (Qiagen, Valencia, Calif.), ChargeSwitch® technology (Invitrogen, Corp., Carlsbad, Calif.), MagaZorb® isolation kits (Cortex Biochem, Inc., San Leandro, Calif.) and NucliSENS® Isolation Kit (bioMérieux, Inc., Durham, N.H.) have also been reported.

Many chemical methods have been utilized for the immobilization of molecules such as nucleic acids on filter membranes. For example, activated paper (TransBind™, Schleicher & Schuell Ltd., Keene, N.H.), carbodimidazole-activated hydrogel-coated PVDF membrane (Immobilin-IAV™, Millipore Corp., Bedford, Mass.), MAP paper (Amersham, Littlechalfont Bucks, Wis.), activated nylon (BioDyne™, Pall Corp., (Glen Cove, N.Y.), DVS- and cyanogen bromide-activated nitrocellulose. Membranes bound with specific ligands are also known such as the SAM2™ Biotin Capture Membrane (Promega) which binds biotinylated molecules based on their affinity to streptavidin or MAC affinity membrane system (protein A/G) (Amicon, Bedford, Mass.). A primary disadvantage of covalent attachment of biomolecules onto activated membranes is that the covalently bound molecules can not be retrieved from the filter membrane.

More recently, glass microfiber has been shown to specifically bind nucleic acids from a variety of nucleic acid containing sources very effectively (e.g., Itoh et al. (1997), *Nucleic Acids Res* 25:1315-1316; Andersson et al (1996), *BioTechniques* 20:1022-1027; U.S. Pat. No. 5,910,246). Under the correct salt and buffering conditions, nucleic acids will bind to glass or silica with high specificity. U.S. Pat. No. 5,234,809 describes a method in which nucleic acids are bound to a solid medium in the form of silica particles, in the presence of a chaotropic agent such as a guanidinium salt, and thereby separated from the remainder of the sample. International published application No. WO 91/12079 describes a method whereby nucleic acid is trapped on the surface of a solid medium by precipitation. Generally speaking, alcohols and salts are used as precipitants. U.S. Pat. No. 6,617,105 describes a method for isolating nucleic acids from cells in which cells are non-specifically or specifically bound to a solid medium, such as glass, silica, latex or polymeric materials, the cells are lysed allowing the DNA to be bound to the same solid phase which is then recovered. A similar process using a porous matrix is described in U.S. Pat. No. 5,653,141.

Nucleic acids or genetic material can be immobilized to a cellulosic-based dry solid support or filter (FTA® filter; FTA® cellulosic filter material; Whatman, plc). See, for example, U.S. Pat. Nos. 5,496,562, 5,756,126, 5,807,527, 6,322,983 and 6,627,226. The solid support described is conditioned with a chemical composition that is capable of carrying out several functions: (i) lyse intact cellular material upon contact, releasing genetic material, (ii) enable and allow for the conditions that facilitate genetic material immobilization to the solid support (probably by a combination of mechanical and chaotrophic), (iii) maintain the immobilized genetic material in a stable state without damage due to degradation, endonuclease activity, UV interference, and microbial attack, and (iv) maintain the genetic material as a support-bound molecule that is not removed from the solid support during any down stream processing (e.g., Del Rio et al. (1995), *BioTechniques* 20:970-974).

The usefulness of the so called FTA® cellulosic filter material described in the above patents has been illustrated for several nucleic acid techniques such as bacterial ribotyping (Rogers and Burgoyne (1997), *Anal Biochem* 247: 223-227), detection of single base differences in viral and human DNA (Ibrahim et al. (1998), *Anal Chem* 70: 2013-2017), DNA databasing (Ledray et al. (1997), *J Emergency Nursing* 23:156-158), automated processing for STR electrophoresis (Belgrader and Marino (1996), L.R.A. 9:3-7; Belgrader et al. (1995), *BioTechniques* 19:427-432), and oligonucleotide ligation assay for diagnostics (Baron et al. (1996), *Nature Biotech* 14:1279-1282).

As illustrated above, various materials and solid media have been and continue to be utilized to provide a base for performing any desired analysis of the genetic material. Those materials include, for example, FTA® filter paper or FTA®-coated materials. In particular, FTA®-coated materials have been successfully utilized for preparing all types of genetic material for subsequent genetic analysis. Genetic material prepared using FTA®-coated materials and FTA® techniques yields highly purified material bound to the cellulosic base filter for the duration of various subsequent applications and amplification reactions. FTA®-coated base filter materials include, but are not limited to Whatman cellulosic BFC-180, 31-ET, glass microfibers, and other similar filter materials known to those of skill in the art.

It is known that high molecular weight genetic material does not release well from any media. For example, it has been shown that nucleic acid or genetic material applied to, and immobilized to, FTA® filters cannot be simply removed, or eluted from the solid support once bound (Del Rio et al. (1995), *BioTechniques* 20:970-974). This is a major disadvantage for applications where several downstream processes are required from the same sample, such a STR profiling and genotyping. This disadvantage has recently been confirmed. Specifically, it has been shown that not all commercial methods are capable of extracting sufficient DNA for use in a whole genome amplification step prior to a quantitative PCR (Q-PCR) reaction (Sjöholm et al. (2007), *Clin Chem* 53:1401-1407). These commercial methods are extremely cumbersome and many hours are required to obtain enough material for use in a Q-PCR reaction.

The difficulty in removing genetic material from FTA® filters has been well recognized in the art, and several techniques have been developed for removing genetic material from FTA® filters. One technique includes the use of chemical methods, such as the use of special buffer compositions (U.S. Pat. No. 6,410,725). This technique, as well as other techniques that rely on the use of chemical methods to release the genetic material, require additional reagents and steps, thus increasing the complexity of the isolation of genetic material. Other techniques include photolysis (U.S. Pat. No. 6,972,329), heat (U.S. Pat. No. 6,645,717) and treatment of the genetic material on the paper for detection (U.S. Pat. No. 6,746,841).

Although the above methods speed up the nucleic acid separation process, a need still exists for methods which are quick and simple to perform, which have higher efficiency, and in particular which are readily amenable to isolating nucleic acids from cells for use in microfluidic environments, such as microfluidic PCR methods.

SUMMARY OF THE INVENTION

The present invention relates to systems for releasing genetic materials from a solid medium. The present invention also relates to methods for releasing genetic materials from a solid medium. The present invention further relates to methods for isolating genetic material from a biological sample.

Thus, in one aspect, the present invention provides a genetic material releasing system comprising a pressure wave emitting device, a chamber and a solid medium in the chamber. The solid medium is configured to adsorb or bind genetic material from a sample added to the chamber. In one embodiment, the adsorption or binding is non-specific. The pressure wave emitting device is configured to emit pressure waves. The solid medium and the chamber are configured so that when a portion of the pressure waves impinge upon the solid medium, a portion of the adsorbed or bound genetic material is released from the solid medium. In one embodiment, the pressure waves are sound waves and the pressure wave emitting device is an acoustic energy emitting device. In one embodiment, the solid medium is any solid material that is capable of adsorbing or binding genetic material. In another embodiment, the solid medium is solid material that includes a coating which is capable of adsorbing or binding genetic material. In a further embodiment, the solid medium is selected from the group consisting of FTA® paper or FTA®-coated materials, silica particles, silica gel particles, glass particles, glass fibers, glass microfibers, glass fiber fleece, cellulosic materials, such as a cellulose based substrates, metallic beads, magnetic beads, metallic particles and magnetic particles. In a further embodiment, the genetic material system further comprises a mechanical energy device. The solid medium and the chamber are configured so that when a portion of the mechanical energy impinges upon the solid medium, a portion of the adsorbed or bound genetic material is released from the solid medium.

In a second aspect, the present invention provides a method for releasing genetic material from a solid medium which has adsorbed or bound genetic material. In accordance with this aspect, the method comprises subjecting a solid medium having genetic material adsorbed or bound thereto to pressure waves to release at least a portion of the genetic material from the solid medium. In one embodiment, the pressure waves are sound waves and the sound waves are produced by an acoustic energy emitting device. In one embodiment, the solid medium is any solid material that is capable of adsorbing or binding genetic material. In another embodiment, the solid medium is solid material that includes a coating which is capable of adsorbing or binding genetic material. In a further embodiment, the solid medium is selected from the group consisting of FTA® paper or FTA®-coated materials, silica particles, silica gel particles, glass particles, glass fibers, glass microfibers, glass fiber fleece, cellulosic materials, such as a cellulose based substrates, metallic beads, magnetic beads, metallic particles and magnetic particles. In a further embodiment, the method for releasing genetic material from a solid medium further comprises subjecting the solid medium to mechanical energy to release at least a portion of the genetic material from the solid medium. The released genetic material can be recovered and stored for future use. Alternatively, the released genetic material can be separated from the solid medium and directly processed for nucleic acid analysis such as PCR reactions. The method is particularly suited for releasing genetic material from a solid medium that can be used in microfluidic PCR techniques for nucleic acid analysis and detection. In addition to causing the release of the genetic material from the solid medium, one additional advantage of the use of acoustic energy in accordance with the present invention is the fragmentation of the DNA by the acoustic energy which makes the DNA better suited for analysis.

In a third aspect, the present invention provides a method for recovering genetic material from a biological sample. In accordance with this aspect, the method comprises contacting a biological sample comprising genetic material with a solid medium, retaining the genetic material with the solid medium, subjecting the solid medium with retained genetic material to pressure waves to release at least a portion of the genetic material from the solid medium and recovering the released genetic material. The genetic material is retained with the solid medium by adsorption or binding.

In one embodiment, the pressure waves are sound waves and sound waves are produced by an acoustic energy emitting device. In one embodiment, the genetic material is free in the biological sample. In another embodiment, the biological sample comprises cells containing the genetic material and the cells are lysed before contacting the biological sample with the solid medium. In an additional embodiment, the biological sample comprises cells containing the genetic material and the cells are lysed while contacting the biological sample with the solid medium. In a further embodiment, the biological sample comprises cells containing the genetic material and the solid medium is capable of lysing the cells. In a still further embodiment, the biological sample comprises cells containing the genetic material and the cells are lysed after contacting the biological sample with the solid medium. In one embodiment, the solid medium is washed to remove non-genetic material prior to releasing the genetic material from the solid medium. In one embodiment, the solid medium is any solid material that is capable of adsorbing or binding genetic material. In another embodiment, the solid medium is a solid material that includes a coating which is capable of adsorbing or binding genetic material. In a further embodiment, the solid medium is selected from the group consisting of FTA® paper or FTA®-coated materials, silica particles, silica gel particles, glass particles, glass fibers, glass microfibers, glass fiber fleece, cellulosic materials, such as a cellulose based substrates, metallic beads, magnetic beads, metallic particles and magnetic particles. In a further embodiment, the method for releasing genetic material from a solid medium further comprises subjecting the solid medium to mechanical energy to release at least a portion of the genetic material from the solid medium.

The released genetic material can be recovered, e.g., separated from the solid medium, and stored for future use.

Alternatively, the released genetic material can be recovered, e.g., separated from the solid medium, and directly processed for nucleic acid analysis such as PCR reactions. The method is particularly suited for releasing genetic material from a solid medium that can be used in microfluidic PCR techniques for nucleic acid analysis and detection. In addition to causing the release of the genetic material from the solid medium, one additional advantage of the use of acoustic energy in accordance with the present invention is the fragmentation of the DNA by the acoustic energy which makes the DNA better suited for analysis.

In a fourth aspect, the present invention provides for a nucleic acid releasing device which comprises an energy emitting device, a chamber and an adsorption substrate, wherein the absorption substrate is within the chamber, wherein the absorption substrate is configured to adsorb nucleic acid from a sample, and wherein the energy emitting device is configured to emit energy, wherein the adsorption substrate and chamber are configured so that when a portion of the energy impinges upon the adsorption substrate, a portion of the adsorbed nucleic acid is released from the adsorption substrate. In one embodiment, the energy emitting device is a pressure wave emitting device. In another embodiment, the pressure wave emitting device is an acoustic energy emitting device. In yet another aspect of this embodiment, the energy is contained in thermal energy. In a further embodiment, the nucleic acid releasing device further comprises a mechanical energy device. The absorption substrate and the chamber are configured so that when a portion of the mechanical energy impinges upon the solid medium, a portion of the adsorbed or bound genetic material is released from the solid medium.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention.

DETAILED DESCRIPTION OF PREFERRED EMBODIMENT

Figure 1:
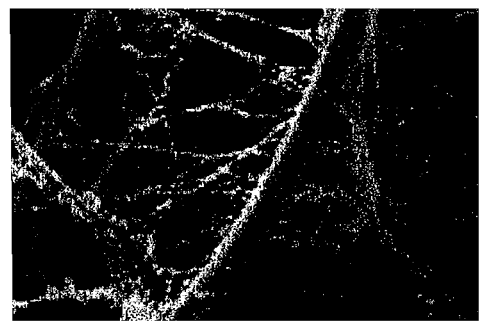
FIG. 1 is an electron micrograph showing DNA entrapped within the FTA® matrix (magnification ×10,000).

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach,* 1984, IRL Press, London, Nelson and Cox (2000), Lehninger, *Principles of Biochemistry* 3rd Ed., W. H. Freeman Pub., New York, N.Y. and Berg et al. (2002) *Biochemistry,* 5th Ed., W. H. Freeman Pub., New York, N.Y., all of which are herein incorporated in their entirety by reference for all purposes.

In one aspect, the present invention provides a genetic material releasing system comprising a pressure wave emitting device, a chamber and a solid medium in the chamber. The solid medium is configured to adsorb or bind genetic material from a sample added to the chamber. The pressure wave emitting device is configured to emit pressure waves in a manner that causes the release of at least a portion of the genetic material from the solid medium. In one embodiment, the pressure waves are sound waves and the pressure wave emitting device is an acoustic energy emitting device.

As used herein, "genetic material" means any nucleic acid, including DNA and RNA. Thus, genetic material may include a gene, a part of a gene, a group of genes, a fragment of many genes, a molecule of DNA or RNA, molecules of DNA or RNA, a fragment of a DNA or RNA molecule, or fragments of many DNA or RNA molecules. Genetic material can refer to anything from a small fragment of DNA or RNA to the entire genome of an organism.

As used herein, the term "chamber" refers to any device to which a sample can be added and treated in accordance with the present invention.

The "solid medium" or "solid substrate" or "solid phase" or "solid matrix" is not critical and can be any solid material generally used by those skilled in the art. A "solid material" or "solid phase material" or "solid phase," as used herein, refers to any material which is insoluble, or can be made insoluble by a subsequent reaction. Any known solid support may be used. Examples of commonly used solid phase materials include, but are not limited to, matrices, particles, micro beads and macro beads free in solution, made of any known material, e.g., cellulose, nitrocellulose, nylon, glass, polyacrylates, mixed polymers, polystyrene, silane polypropylene, silica gel, metal, such as non-magnetic and magnetic beads and particles. See, for example, U.S. Pat. Nos. 4,358,535, 4,797,355, 5,237,016, 5,652,141, 6,645,717, 6,617,105, 6,627,226, 7,214,780 and 7,294,489. In some embodiments, the solid substrate may include a magnetic bead, a matrix, a particle, a polymeric bead, a chromotagraphic resin, filter paper, a membrane or a hydrogel.

The solid material may be capable of adsorbing or binding the genetic material directly or it may be coated with a material that is capable of adsorbing or binding the genetic material. As used herein, adsorption or binding refers to the immobilization of genetic material on solid phases through ionic interactions, hydrophobic interactions, covalent interactions, chelation and the like. The interactions may be direct or they may be indirect, such as through one or more linkers, as is well known to the skilled artisan. Among the advantages of solid phase systems is that they can be washed with relative ease to remove cellular components other than the bound genetic material.

One solid medium that has found significant use for collecting and storing DNA samples is FTA® solid substrates. These solid substrates also contain chemicals that lyse cells, denature proteins and protect the genetic material from enzymatic or other degradation. FIG. 1 is an electron micrograph showing DNA entrapped within the FTA® matrix (magnification ×10,000). As discussed above, it is well known that it is difficult to remove the genetic material from FTA® solid substrates.

The pressure wave emitting device may be any device the is capable of generating pressure waves within the chamber such that the impingement of the pressure waves on the solid medium causes a release of at least a portion of the genetic material. Suitable pressure wave emitting devices are well known to the skilled artisan. Examples of pressure wave emitting devices include, but are not limited to, a transducer that is a vibrating type or a transducer that is an oscillating device. These devices are activated to generate pressure waves in the chamber.

In one embodiment, the pressure wave emitting device is an acoustic energy emitting device. The acoustic energy emitting device produces acoustic energy this is used to release genetic material from a solid support. Any device that generates sound waves can be used as a source of acoustic energy. Such devices include, but are not limited to, ultrasonic transducers, piezoelectric transducers, magnorestrictive transducers and electrostatic transducers. Suitable devices are well known in the art including such commercially available devices as Sonicator 4000 (Misonix, Inc., Farmingdale, N.Y., USA), Microson® Sonicator Microprobe or Micro Cup Horn (Kimble/Kontes, Vineland, N.J., USA) and Covaris™ Adaptive Focused Acoustics (Nexus Biosystems, Poway, Calif., USA). Other suitable devices are described in U.S. Pat. Nos. 6,881,541 and 6,878,540 and in U.S. Patent Application Publication No. 2007/0170812. One advantage of using acoustic energy to release the genetic material from the solid support is that not only is the genetic material released, but the genetic material is also sheared to generate fragments of genetic material.

Figure 3A:
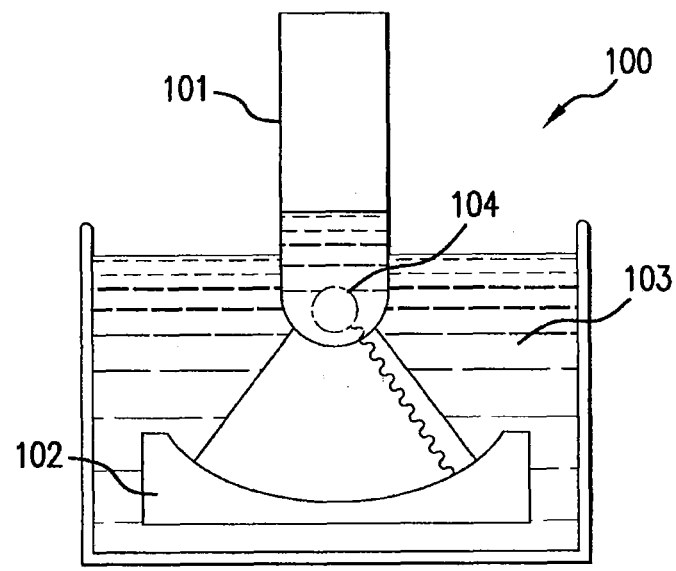
FIG. 3A illustrates an adaptive focused acoustic system that can be used to send acoustic energy wave packets into a sample container that may contain genetic material bound to a solid phase.
Figures 3B, 3C:
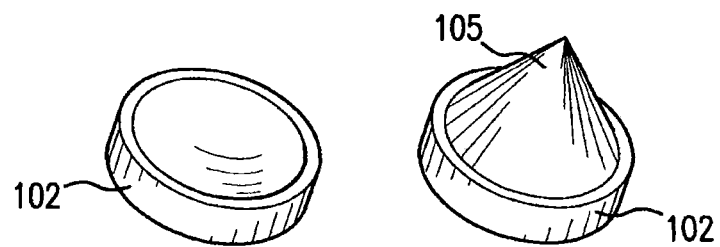
FIG. 3B illustrates the transducer shown in FIG. 3A.
FIG. 3C illustrates the transducer shown in FIG. 3B with beam of energy.
Figure 2A:
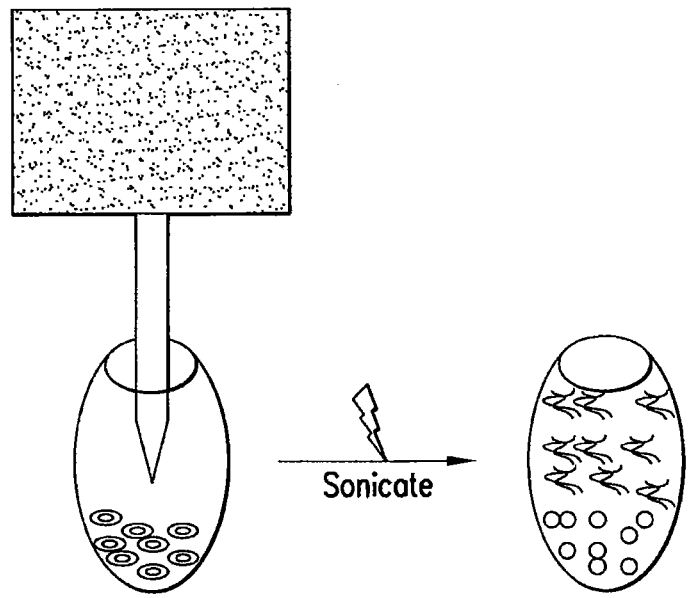
FIG. 2A is an illustration of one embodiment of the present invention in which genetic material is bound to beads and the sample is subjected to sonication to release the genetic material from the beads.
Figure 2B:
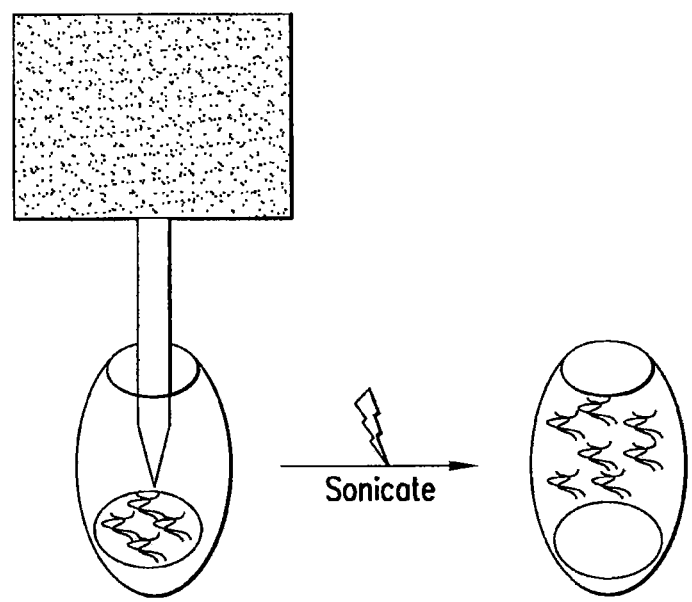
FIG. 2B is an illustration of another embodiment of the present invention in which genetic material is bound to cellulosic substrate and the sample is subjected to sonication to release the genetic material from the cellulosic substrate.
Figure 4:
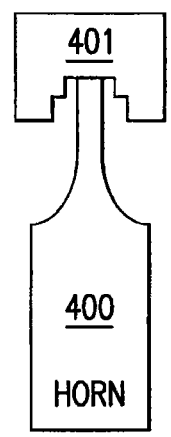
FIG. 4 is an illustration of a non-contact acoustic system.

FIGS. 2-4 show illustrations of the acoustic energy devices referenced above. Specifically, FIGS. 2A and 2B illustrate an acoustic energy device which includes a probe which is inserted into a liquid in contact with the solid medium. Contact sonicators, i.e., sonicators placed in the sample containing chamber, are examples of such an acoustic energy device. FIG. 3A illustrates an acoustic energy emitting device 100 which includes a transducer 102 that focuses acoustic energy into a chamber 101 that is inserted into a liquid 103 in contact with the device. In the non-limiting embodiment shown in FIG. 3A, the acoustic energy emitting device is a dish-shaped transducer 102 that focuses the acoustic energy to a focal zone 104 in the chamber 101. FIG. 3B is a further illustration of transducer 102. FIG. 3C illustrates transducer 102 with beam of energy 105. FIG. 4 illustrates a non-contact acoustic energy emitting device 400 in which the device is not in contact with the sample but is in direct contact with the chamber 401. The system can be used to transmit acoustic energy through the sample chamber. In another aspect, the acoustic energy emitting device is positioned sufficiently close to the chamber such that the acoustic energy emitted from the acoustic energy emitting device causes the release of at least a portion of genetic material from the solid medium.

In a further embodiment, genetic material releasing system further comprises a mechanical energy device. The mechanical energy device is configured in a manner so that the mechanical energy causes the release of at least a portion of the genetic material from the solid medium. Any suitable mechanical energy device can be used and such devices are well known to the skilled artisan. Examples of mechanical energy devices include, but are not limited to, devices which cause vibration, vortexing and homogenization. For example, Pro Scientific offers a variety of homogenizers (e.g. Pro 200-Pro 400), VWR Scientific offers a variety of vortexers (e.g.

MV-1 Mini Vortexer), and BioSpec Products, Inc. offers a handheld ultrasonic homogenizer (Sonozap), all of which can be used to provide the energy necessary to liberate DNA from a solid medium.

In a second aspect, the present invention provides a method for releasing genetic material from a solid medium which has adsorbed or bound genetic material. In accordance with this aspect, the method comprises subjecting a solid medium having genetic material adsorbed or bound thereto to pressure waves to release at least a portion of the genetic material from the solid medium. The genetic material and solid medium are as described herein. The pressure waves are generated using a pressure wave emitting device as described herein. In one embodiment, the pressure wave emitting device is an acoustic energy emitting device, as described herein. The pressure waves are generated in a chamber containing the solid medium with the genetic material for a time sufficient to release at least a portion of the genetic material from the solid medium. The length of time is empirically determined on the basis of the amount of genetic material that may be needed for downstream processing. This determination is well within the skill in the art.

FIGS. 2A and 2B illustrate embodiments of this method of the present invention. A chamber is provided which contains a solid medium having genetic material adsorbed or bound thereto. The DNA is bound to a solid medium in a conventional manner. In the illustrated examples, the solid medium may be beads (FIG. 2A) which may be non-magnetic or magnetic or FTA® paper (FIG. 2B). The solid medium having the adsorbed or bound DNA is exposed to ultrasonic waves to physically disrupt the interaction of the DNA with the solid medium. FIGS. 2A and 2B show the use of a micro tip probe sonicator to produce ultrasonic energy in a liquid via a probe introduced directly into the liquid. The sample is sonicated and the sonication results in the release of at least a part of the genetic material from the solid medium.

In a further embodiment, the method further comprises subjecting the sample to mechanical energy to cause the release of at least a portion of the genetic material associated with the solid medium. The mechanical energy, as described herein, is generated in a chamber containing the solid medium with the genetic material for a time sufficient to release at least a portion of the genetic material from the solid medium. The length of time is empirically determined on the basis of the amount of genetic material that may be need for downstream processing. This determination is well within the skill in the art. The use of mechanical energy in conjunction with the use of pressure waves, particularly acoustic energy, enables using a lower amount of pressure waves or acoustic energy in releasing the genetic material.

In other embodiments, the sample comprises cells and the method further comprises first lysing the cells before subjecting the sample to the pressure waves. In some embodiments, the lysis is performed by chemical lysis. Typical chemical lysing agents fall into several categories, such as enzymes, and detergents. Lysosyme is an enzyme that hydrolytically attacks the cell walls of many bacteria; trypsin is a protease enzyme that breaks the cell membrane of most eukaryotic cells. Other proteases with specificity for certain peptide sequences can be employed and are preferred if the target moiety is liable to certain proteases. Proteinase K is often used because it also digests nuclear proteins and host cell enzymes that may interfere with polymerase chain reaction (PCR). For eucaryotic cells, detergents such as Triton X-100 or sodium dodecyl sulfate solubilize the cell membrane and release intracellular contents. Commercial cell lysis products can be used to lyse cells in the cellular sample. Such commercial cell lysis products include, but are not limited to, Poppers Cell Lysis Reagents (Pierce, Rockville, Ill., USA), Wizard® Genomic DNA Purification Kit (Promega Corp., Madison, Wis., USA), lysis solutions from Qiagen, Inc. (Valencia, Calif., USA), and Cell Lysis Solution (Spectrum Chemical and Laboratory Products, Gardena, Calif., USA). Alternatively, acoustic energy, such as described herein and used to release the genetic material from the solid phase, can be used to lyse cells in a cellular sample.

The lysis may occur prior to contacting the sample with the solid medium. In this embodiment, the sample could be treated to remove contaminants as is well known to the skilled artisan. Alternatively, the solid medium may contain components that lyse intact cellular material upon contact thereby releasing the genetic material which is then adsorbed or bound to the solid medium. One example of such a solid medium is FTA® paper or FTA®-coated materials.

The released genetic material can be recovered, e.g., separated from the solid medium, and stored for future use. Alternatively, the released genetic material can be recovered, e.g., separated from the solid medium, and directly processed for nucleic acid analysis such as PCR reactions.

Experimental data has been generated to determine the efficiency of sonication versus the methods recommended by the manufacturer of FTA® paper. In the experiment detailed below, Whatman FTA® paper is the solid substrate used to bind DNA after cells lyse upon contact with the paper. The general procedure for DNA elution from the paper is incubating the paper in TE buffer for 10-15 minutes, vortexing a few times, and then centrifuging the sample for 1 minute at 13,000 rpm. To increase the efficiency of elution of DNA from the FTA® paper the manufacturer has also recommended incubating the paper for 5 minutes in a pH 13 solution and neutralizing for 15 minutes with a second buffer, then centrifuge for 1 minute at 13,000 rpm. Both methods were tested for efficiency and compared with sonicating the FTA® paper in the presence of water or TE buffer in accordance with one embodiment of the present invention.

Figure 5A:
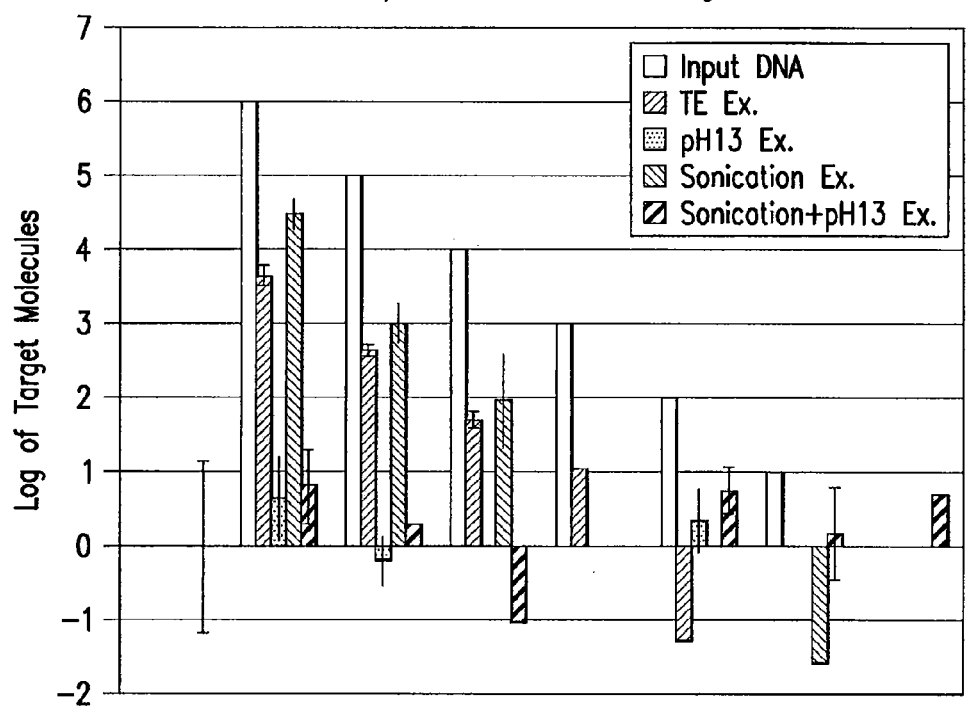
FIG. 5A shows a comparison of different extraction methods for FTA® paper for gram positive microorganism.
Figure 5B:
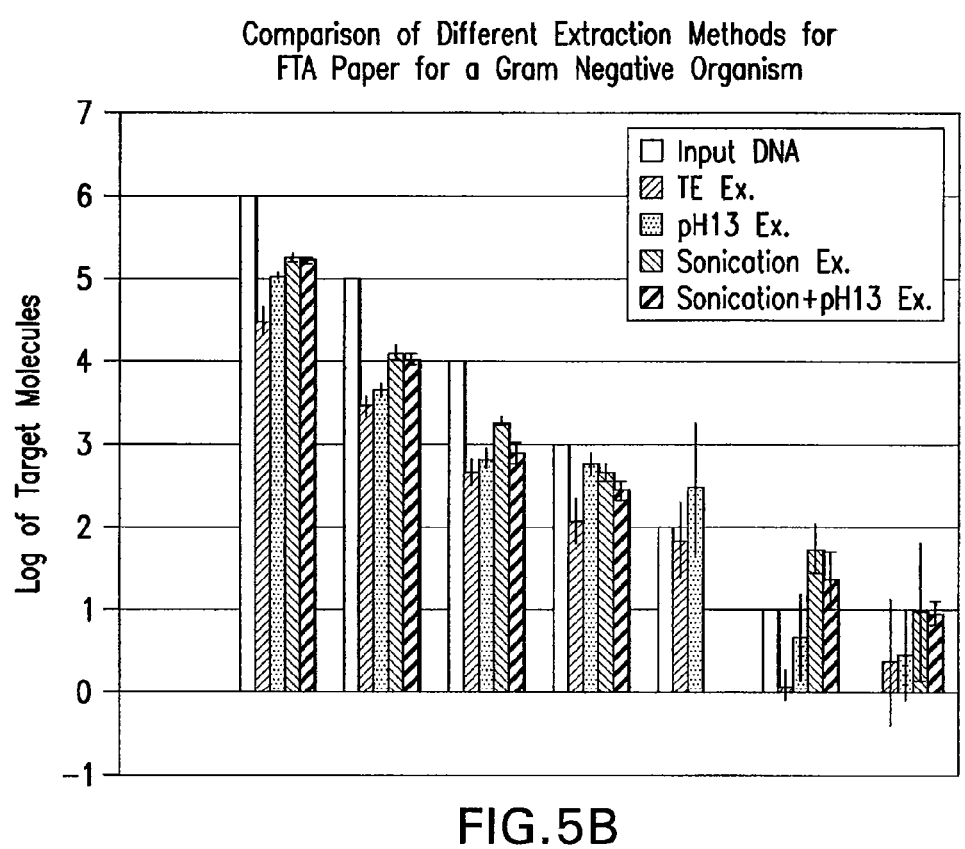
FIG. 5B shows a comparison of different extraction methods for FTA® paper for gram negative microorganism.

As shown in FIGS. 5A and 5B, the sonication results are significantly better than that of altering pH or TE elution. FIG. 5A shows a comparison of different extractions methods for FTA® paper for gram positive microorganism. The extraction methods examined included TE (10 mM Tris-HCl, 1 mM EDTA; pH 7.5) extraction, high pH (i.e., pH 13), sonication (3×5 sec pulses at 20 kH) and sonication with high pH. In FIG. 5A, it is clear that treatment with high pH is deleterious to the DNA, and that sonication is clearly more efficient than either TE elution or high pH elution.

FIG. 5B shows a comparison of different extraction methods for FTA® paper for gram negative microorganism. The extraction methods examined included TE extraction, high pH (i.e., pH 13), sonication and sonication with high pH. In FIG. 5B, sonication is about an order of magnitude more efficient at eluting DNA when compared with the TE elutions, and is slightly better than the pH 13 elutions in most cases.

The data in FIGS. 5A and 5B reflect the improved efficiency of eluting DNA from FTA® paper when sonication is used as the elution method.

In a third aspect, the present invention provides a method for recovering genetic material from a biological sample. In accordance with this aspect, the method comprises contacting a biological sample comprising genetic material with a solid medium, retaining the genetic material with the solid medium, subjecting the solid medium with retained genetic material to pressure waves to release at least a portion of the genetic material from the solid medium and recovering the released genetic material. The solid medium is as described herein. In one embodiment, the genetic material is free in the biological sample. In another embodiment the biological sample comprises cells. The biological sample comprising cells may be a blood sample, a urine sample, a saliva sample, a sputum sample, a cerebrospinal fluid sample, a body fluid sample, a tissue sample, or the like. The genetic material is retained with the solid medium by adsorption or binding. The biological sample is contacted with the solid medium, such as the solid media described herein, using conventional techniques well known to the skilled artisan.

The pressure waves are generated using a pressure wave emitting device as described herein. In one embodiment, the pressure wave emitting device is an acoustic energy emitting device, as described herein. The pressure waves are generated in a chamber containing the solid medium with the genetic material for a time sufficient to release at least a portion of the genetic material from the solid medium as described herein.

In another embodiment, the biological sample comprising cells containing the genetic material is first treated to lyse the cells before contacting the biological sample with the solid medium as described herein. In an additional embodiment, the biological sample comprises cells containing the genetic material and the cells are lysed while contacting the biological sample with the solid medium as described herein. In a further embodiment, the biological sample comprises cells containing the genetic material and the solid medium is capable of lysing the cells. In a still further embodiment, the biological sample comprises cells containing the genetic material and the cells are lysed after contacting the biological sample with the solid medium. In one embodiment, the solid medium is washed to remove non-genetic material prior to releasing the genetic material from the solid medium.

In a further embodiment, the method for releasing genetic material from a solid medium further comprises subjecting the solid medium to mechanical energy as described herein to release at least a portion of the genetic material from the solid medium.

The released genetic material can be recovered, e.g., separated from the solid medium, and stored for future use or used in downstream applications as described herein or as well known to the skilled artisan.

In a fourth aspect, the present invention provides for a nucleic acid releasing device comprises an energy emitting device, a chamber and an adsorption substrate, wherein the absorption substrate is within the chamber, wherein the absorption substrate is configured to adsorb nucleic acid from a sample, and wherein the energy emitting device is configured to emit energy, wherein the adsorption substrate and chamber are configured so that when a portion of the energy impinges upon the adsorption substrate, a portion of the adsorbed nucleic acid is released from the adsorption substrate. The nucleic acid may be DNA or RNA. The adsorption substrates are well known to the skilled artisan and include those solid media described herein which adsorb nucleic acids. In one embodiment, the energy emitting device is a pressure wave emitting device as described herein. In another embodiment, the pressure wave emitting device is an acoustic energy emitting device as described herein. In yet another aspect of this embodiment, the energy is contained in thermal energy, such as, for example, heat produced by pressure waves within the chamber. In a further embodiment, the nucleic acid releasing device further comprises a mechanical energy device as described herein. The absorption substrate and the chamber are configured so that when a portion of the mechanical energy impinges upon the solid medium, a portion of the adsorbed or bound genetic material is released from the solid medium as described herein.

There are several advantages to the method of the present invention versus conventional methods of eluting DNA from a solid substrate. For example, the DNA is liberated from a solid material in seconds when acoustic energy is applied, versus minutes to hours when other methods are utilized. In addition, DNA is eluted more efficiently when acoustic energy is used versus traditional methods. Recovery of the DNA can be greater than an order of magnitude higher when using acoustic energy versus conventional elution methods. Further, the DNA is also in more manageable fragments for down stream applications when acoustic energy is applied to liberate DNA from a solid matrix.

The method is particularly suited for releasing genetic material from a solid medium that can be used in microfluidic PCR techniques for nucleic acid analysis and detection. In addition to causing the release of the genetic material from the solid medium, one additional advantage of the use of acoustic energy in accordance with the present invention is the fragmentation of the DNA by the acoustic energy which makes the DNA better suited for analysis.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. A method of recovering genetic material from a biological sample which comprises the steps of:
  (a) contacting a biological sample comprising genetic material with a solid medium;
  (b) covalently binding the genetic material with the solid medium;

(c) subjecting the solid medium with bound genetic material to a pressure wave to release at least a portion of the genetic material from the solid medium;

(d) recovering the released genetic material; and (e) storing the recovered genetic material or subjecting the recovered genetic material to at least one nucleic acid analysis process.

2. The method of claim 1, wherein the pressure wave is a sound wave.

3. The method of claim 2, wherein the sound wave is produced by an acoustic energy emitting device.

4. The method of claim 3, wherein the acoustic energy emitting device is an ultrasonic transducer, a piezoelectric transducer, a magnorestrictive transducer or an electrostatic transducer.

5. The method of claim 3, wherein the solid medium is subjected to the acoustic energy by inserting an acoustic energy emitting device into a liquid in contact with the solid medium.

6. The method of claim 5, wherein the solid medium is subjected to the acoustic energy by inserting a sonicator into a liquid in contact with the solid medium.

7. The method of claim 3, wherein the solid medium is subjected to the acoustic energy by inserting a chamber holding the solid medium into a liquid in contact with an acoustic energy emitting device.

8. The method of claim 7, wherein the solid medium is subjected to the acoustic energy by inserting a chamber holding the solid medium into a liquid in contact with a transducer that focuses acoustic energy.

9. The method of claim 8, wherein the solid medium is subjected to the acoustic energy by inserting a chamber holding the solid medium into a liquid in contact with a dish-shaped transducer.

10. The method of claim 3, wherein the acoustic energy emitting device is in direct contact with a chamber.

11. The method of claim 3, wherein the acoustic energy emitting device is positioned sufficiently close to a chamber such that the acoustic energy emitted from the acoustic energy emitting device causes the release of at least a portion of genetic material from the solid medium.

12. The method of claim 1, wherein the solid medium is selected from the group consisting of filter paper, silica particles, silica gel particles, glass particles, glass fibers, glass microfibers, glass fiber fleece, polymeric materials, cellulosic materials, metallic beads, magnetic beads, metallic particles and magnetic particles.

13. The method of claim 12, wherein the cellulosic material is a cellulose based substrate.

14. The method of claim 1, wherein the biological sample comprises cells containing the genetic material and the cells are lysed before, while or after contacting the biological sample with the solid medium.

15. The method of claim 14, wherein the solid medium is selected from the group consisting of filter paper, silica particles, silica gel particles, glass particles, glass fibers, glass microfibers, glass fiber fleece, polymeric materials, cellulosic materials, metallic beads, magnetic beads, metallic particles and magnetic particles.

16. The method of claim 15, wherein the cellulosic material is a cellulose based substrate.

17. The method of claim 1, wherein the biological sample comprises cells containing the genetic material and the solid medium is capable of lysing the cells.

18. The method of claim 17, wherein the solid medium is selected from the group consisting of filter paper, silica particles, silica gel particles, glass particles, glass fibers, glass microfibers, glass fiber fleece, polymeric materials, cellulosic materials, metallic beads, magnetic beads, metallic particles and magnetic particles.

19. The method of claim 18, wherein the cellulosic material is a cellulose based substrate.

20. The method of claim 1, which further comprises subjecting the solid medium to mechanical energy.

21. The method of claim 20, wherein the solid medium is subjected to the mechanical energy and the pressure wave at the same time.

22. A method of recovering genetic material from a biological sample which comprises the steps of:

(a) contacting a biological sample comprising genetic material with a solid medium;

(b) covalently binding the genetic material with the solid medium;

(c) subjecting the solid medium with bound genetic material to a pressure wave to release at least a portion of the genetic material from the solid medium;

(d) recovering the released genetic material; and (e) using the recovered genetic material in a polymerase chain reaction.

* * * * *